United States Patent [19]

Kobayashi et al.

[11] Patent Number: 4,840,620

[45] Date of Patent: Jun. 20, 1989

[54] PORTABLE PUMP FOR INFUSING MEDICINE INTO A LIVING BODY

[75] Inventors: Susumu Kobayashi; Kazumasa Satoh, both of Fujinomiya, Japan

[73] Assignee: Terumo Corporation, Tokyo, Japan

[21] Appl. No.: 33,772

[22] Filed: Apr. 3, 1987

[30] Foreign Application Priority Data

Apr. 7, 1986 [JP] Japan .................................. 61-78288

[51] Int. Cl.⁴ .............................................. A61M 5/00
[52] U.S. Cl. .................................... 604/246; 604/153; 604/131
[58] Field of Search ........................ 604/123, 153–155, 604/131, 246, 251, 253, 255

[56] References Cited

U.S. PATENT DOCUMENTS

| | | | |
|---|---|---|---|
| 4,217,993 | 8/1980 | Jess et al. | 604/123 |
| 4,256,437 | 3/1981 | Brown | 604/123 |
| 4,261,360 | 4/1981 | Perez | 604/123 |
| 4,496,346 | 1/1985 | Mosteller | 604/123 |
| 4,642,098 | 2/1987 | Lundquist | 604/123 |
| 4,710,166 | 12/1987 | Thompson et al. | 604/123 |

Primary Examiner—John D. Yasko
Assistant Examiner—Gene B. Kartchner
Attorney, Agent, or Firm—Staas & Halsey

[57] ABSTRACT

A portable infusion pump for delivering medicine to a living body has a roller pump for infusing solutions by use of a motor, a driving circuit for driving the motor in response to a control signal, and a flow rate control for generating the control signal. The flow rate control includes a manual operating unit for manually setting a value of a speed of the motor, a speed setting unit for generating a digital signal associated with the value set by the manual operating unit, and a control signal output unit for generating the control signal associated with the digital signal delivered from the speed setting unit. Accordingly, the flow rate thus set clearly corresponds to an actual flow rate, thus facilitating the control of the liquid flow rate.

5 Claims, 2 Drawing Sheets

4,840,620

PORTABLE PUMP FOR INFUSING MEDICINE INTO A LIVING BODY

BACKGROUND OF THE INVENTION

1. Field of the Invention

The present invention relates to a portable infusion pump, and in particular, to a portable infusion pump for supplying medicine such as a liquid having a high caloric value to a living body, for example.

2. Description of the Prior Art

A portable infusion pump which can be carried, for example, on a body of a patient and which transports medicine is required to be of a small size and of a light weight. Consequently, control circuitry for controlling a motor of the pump is advantageously configured in a simple structure to the extent possible.

A direct current (DC) motor is suitable for a small-sized apparatus; furthermore, since a DC motor can be easily controlled in motor speed, it is particularly advantageous for a portable infusion pump which needs to control the flow rate of a liquid to be supplied. In general, conventional control apparatus for controlling the flow rate of liquid uses a variable resistor to control the motor speed. However, the adjusting precision of such a variable resistor is relatively coarse and there does not exist a clear one-to-one correspondence between the position of an adjusting slider and the motor speed, which leads to an insufficient reproducibility. Namely, the correspondence cannot be fixedly determined between the flow rate, or a flowing volume per unit period of time, of the liquid transported by the pump and the position of the slider of the variable resistor, and hence a satisfactory reproducibility cannot be attained.

As a result, in the conventional apparatus for controlling the liquid flow rate, the scale marks of the control for adjusting the flow rate indicate only approximated targets, namely, it is difficult to indicate a digit representative of an appropriate setting value.

Moreover, when using a variable resistor, there may not exist a linear relationship between the positions of the adjusting slider and the speed of the motor. In order to design scale marks of the control for adjusting the flow rate to represent directly the flow rate, the scale marks are not distributed with a uniform interval between adjacent ones, which leads to a disadvantage that the adjusting operation cannot be easily achieved.

As well known, as a compact infusion pump for medicine to be used to supply medicine to an organism, there have been used a roller pump and a finger pump having a tube not exposed to the external environment thereof so as to prevent a chance of an infection. Since the pump is required to be of a small size, it is difficult to install in such an infusion pump an apparatus for actually measuring the flow rate.

As can be clear from this situation, in a case where such a compact infusion pump is used, it has been considerably difficult to measure the flow rate of nutritional solutions and other intravenous solutions actually flowing through the liquid transporting tube and further to obtain a setting value of the flow rate.

SUMMARY OF THE INVENTION

It is therefore an object of the present invention to provide a liquid transporting pump for appropriately indicating a setting value of the flow rate of a liquid to be transported, thereby solving the problem of the prior art technology.

An infusion pump of the present invention includes pump means having a pump for transporting a liquid, driving means for driving the motor in response to a control signal, and flow rate controlling means for generating the control signal. The flow rate controlling means comprises manual operating means for manually setting a value of the speed of the motor, speed setting means for generating a digital signal associated with the value set by the manual operating means, and control signal output means of generating a control signal corresponding to the digital signal delivered from the speed setting means to deliver the control signal to the driving means.

According to an aspect of the present invention, the manual operating means includes an indication for indicating a flow rate of liquid infusion associated with the speed of the motor.

According to another aspect of the present invention, the speed setting means includes DIP code switch means for generating a digital signal.

According to still another aspect of the present invention, the pump means comprises a roller pump, which is connected to the motor.

According to a further aspect of the present invention, the control signal output means includes an operational amplifier having an input adapted for receiving the digital signal generated by DIP code switch means and another input to which a reference voltage is supplied.

BRIEF DESCRIPTION OF THE DRAWINGS

The objects and features of the present invention will become more apparent from the consideration of the following detailed description taken in conjunction with the accompanying drawings, in which.

DESCRIPTION OF THE PREFERRED EMBODIMENT

Figure 1:
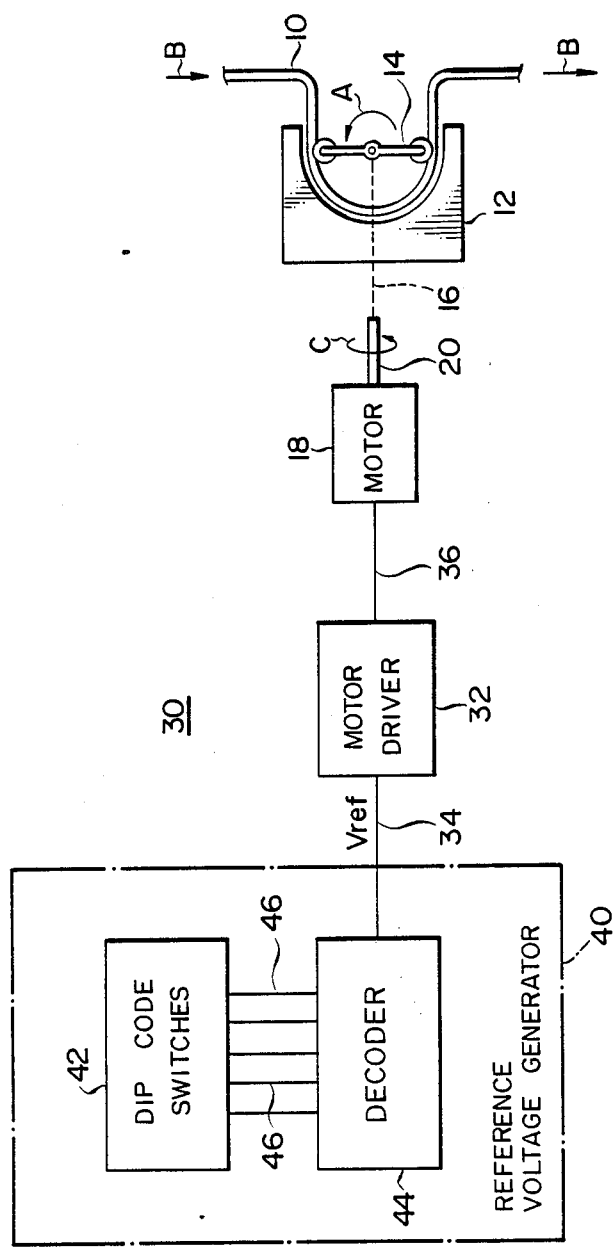
FIG. 1 is a schematic block diagram illustrating an embodiment in which an infusion pump of the present invention is applied to a portable infusion pump to be carried on a body of a patient.

Referring now to FIG. 1, in this embodiment, the present invention is applied to a portable liquid infusion pump which can be carried, for example, on a body of a patient and which delivers medicine such as hyperalimentation solutions to the living body. At an intermediate point of a flexible tube 10 for transporting the medicine from a source of the medicine to be transported, there is disposed a roller pump 12 in this embodiment. When a rotor 14 turns in the direction of an arrow A, the position pressing the tube 10 advances, which transports the medicine in the direction of an arrow B so as to be injected in the living body at a slow rate. In place of such a roller pump 12, a finger pump may be used.

In this emodiment, a shaft 16 of the rotor 14 is mechanically coupled to a shaft 20 imparting torque of a DC motor 18 as conceptually indicated with a broken line and hence is rotated in the direction of an arrow C when the motor 18 is subjected to a driving control by a motor control circuit 30. A flow rate, and hence the speed of the motor 18 can be set to a desired value by the motor control circuit 30.

The DC motor 18 receives power from and is driven by a motor driver 32 of the motor control circuit 30. The motor driver 32 is a motor driver of an electronic governor type for stationarily retaining the speed of the motor 18 at a desired value. A reference voltage Vref as a reference for the speed is delivered from a reference voltage generator 40 to a control input 34 of the driver 32.

The reference voltage generator 40 of this embodiment comprises dual in-line package (DIP) code switches 42 and a decoder 44. In this embodiment, as the DIP code switches 42, ordinary rotary-type switches having a control for manually setting a decimal value are advantageously used. In this embodiment, the flow rate can be set in a range from a decimal value of 0 to 190 milliliter per hour (ml/H).

The DIP code switches 42 are provided with a visual indication representative of the flow rate of a liquid to be transported by the pump 12, namely, scale marks are provided in association with the control knobs thereof. In the case of the embodiment, digits ranging from 00 to 19 are indicated for scale marks associated with the flow rate. The scale marks function as indicating a flow rate by the setting position of the rotary-type control.

In general, the flow rate of a liquid flowing through the tube 10 depends on the cross section of the tube 10 and the flow speed; however, since the motor control circuit 30 is designed dedicatedly for the pump 12 in this embodiment, the specifications of the tube 10 used with the pump 12 are uniquely determined and hence the flow rate of the liquid can also be pointed with a scale mark on the DIP code switches 42. Naturally, in a case where a plurality of tubes having different cross sections are used, plural sorts of scale marks of different scales may be disposed corresponding to the kinds of tubes. Or, there may be provided scale marks simply indicating the speed of the pump 12.

The DIP code switches 42 convert the setting value of the flow rate set with a decimal value by use of the control knobs into a binary-coded decimal (BCD) real code to produce the real code from a parallel output 46. The real code is supplied to the decoder 44, which in turn generates an analog voltage as a reference voltage Vref corresponding to the real code to supply the reference voltage to the output 34. The reference voltage Vref is delivered to the motor driver 32, which in turn rotates the DC motor 18 at a rotary speed associated with the target value of the flow rate set by the DIP code switches 42.

The roller pump 12 has a characteristic that a flow rate f is obtained in proportion to the speed of the rotor 14. In addition, the DC motor 18 develops a rotary speed proportional to a supply voltage 36. Consequently, there exists a linear correspondence between the reference voltage Vref of the control line 34 and the flow rate f of the tube as follows;

$$f = a_1 \cdot V_{ref} + b_1 \quad (1)$$

where $a_1$ and $b_1$ are constants.

On the other hand, since the reference voltage Vref generated by the reference voltage generator 40 is proportional to the setting value n (for example, 0 or a positive integer up to 19) of the DIP code switches 42, if the proportional constants are $a_2$ and $b_2$, $$V_{ref} = a_2 \cdot n + b_2 \quad (2)$$

results. Consequently, from these expressions, the flow rate f is proportional to the setting value n of the DIP code switches 42 as follows;

$$f = a_3 \cdot n + b_3 \quad (3)$$

where, $a_3$ and $b_3$ are constants to be set to arbitrary values according to the circuit design of this system. As described above, in this system, there exists a clear one-to-one correspondence between the flow rate of the pump 12 and the setting value of the DIP code switches 42.

Figure 2:
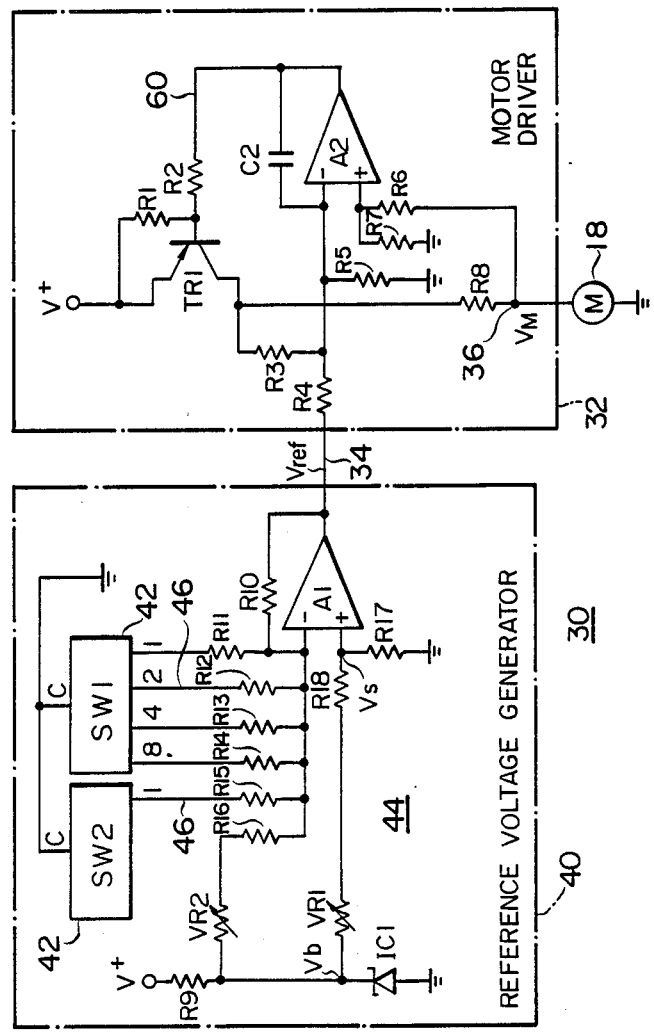
FIG. 2 is a schematic circuit diagram depicting a specific example of a circuit configuration of the embodiment shown in FIG. 1.

Referring now to FIG. 2 showing a specific circuit configuration example of the embodiment of FIG. 1, the reference voltage generator 40 includes an operational amplifier A1 having an inverting input (−) to which BCD code outputs 46 from a switch SW1 and a switch SW2 constituting the DIP code switches 42 are connected via registers R11–R15, as shown in FIG. 2. A non-inverting input (+) of the operational amplifier A1 is supplied with a voltage Vs associated with an essentially constant voltage Vb due to a voltage reference IC1, namely, the voltage Vs is delivered from a voltage source V+ through resisters R9 and R18 and a variable resistor VR1. Incidentally, in FIG. 2, the components like those of FIG. 1 are assigned with the same reference numerals.

The operational amplifier A1, the resistors R10–R18, and the variable resistors VR1 and VR2 constitute a decoder 44. Voltages supplied to the non-inverting input (+) and the inverting input (−) can be manually adjusted by use of the variable resistors VR1 and VR2, respectively. The variable resistor VR2 and the resistor R16 constitute a circuit for defining a bias of the reference voltage Vref, namely, the constant $b_3$ of the expression (3). In addition, the variable resistor VR1 and the resistors R17 and R18 form a circuit defining the constant $a_3$ of the expression (3), namely, the amount of change of the reference voltage Vref for each setting step to be described later.

The motor driver 32 includes a bridge for detecting a difference between the reference voltage Vref and a voltage VM induced in the motor 18. The bridge is constituted with resistors R3, R5 and R8 and an equivalent armature resistance M of the motor 18. The driver 32 includes an operational amplifier A2 having a non-inverting input (+), which is connected to the voltage dividing resistors R6 and R7 so as to input the output voltage VM from the bridge within the in-phase, rated input voltage range as shown in FIG. 2.

The operational amplifier A2 and a capacitor C2 constitute an error amplifier which generates an error voltage associated with the difference voltage for driving the motor 18. An output 60 therefrom is connected to the base of a transistor TR1 via a the resistor R2, whereas the collector of the transistor TR1 is connected via the resistor R8 to an output terminal 36 of the motor driver 32. Namely, the transistor TR1 and the resistors R1 and R2 configure a power amplifier for driving the motor 18.

When the motor 18 is driven, a back-electromotive force is generated to effect a control to set the voltage VM associated with the back-electromotive force and the reference voltage Vref to the same value in any case. As a consequence, the motor 18 is retained at a rotary speed set by the reference voltage Vref independently of the variation in a load thereof.

In this embodiment, the DIP code switches SW1 and SW2 can set a 2-digit integer n=00-19 (n is referred to as a setting step). These switches SW1 and SW2 selectively ground an end of the resistors R11-R15 depending on the numeric value n. The resistors R10 and R11-R15 change the gain of the operational amplifier A1 in the following ratio according to the setting step.

$$R11=R10, R12=R10/2, R13=R10/4, R14=R10/8, R15=R10/10.$$

Consequently, the voltage Vref of the output 34 of the reference voltage generator 40 is determined by the following expression;

$$Vref=(R10/R)Vs+Vs+(R10/Ra)(Vs-Vb) \quad (4)$$

where, $R=R10/n$, $(n=0, 1, 2, \ldots, 19)$ $$Ra=R16+VR2,$$

$$Vs=[R17/(R17+R18+VR1)]Vb.$$

In the portable liquid transporting pump 12 of this embodiment, when the circuitry is adjusted such that the voltage Vs at the non-inverting input (+) of the operational amplifier A1 is equivalent to the flow rate of 10 ml/H and if the control knobs of the DIP switches 42 are operated in the range 00-19, the flow rate can be set in the range 10-190 ml/H.

In this embodiment as described above, since the setting of the flow rate is effected by use of a DIP switch in place of a variable resistor used in the conventional apparatus, there exists a clear correspondence between the flow rate thus set and the actual flow rate. Furthermore, the setting of the flow rate is stepwise conducted according to the unit of flow rate and hence a satisfactory reproducibility is obtained. Consequently, the portable infusion pump of the embodiment removes the actual measurement of the flow rate and the conversion of the rotary speed of the pump to obtain a flow rate which were necessary in the prior art technology, and therefore the amount of a liquid to be transported can be easily controlled.

Moreover, the circuit configuration is simple and the flow rate setting section also functions as an indicator; consequently, the present invention is advantageous with respect to the space factor and the price of the apparatus when applied to a small-sized apparatus such as a portable liquid transporting pump.

In summary, the infusion pump in accordance with the present invention enables setting the flow rate by use of a digital switch with the flow rate setting value indicated, the flow rate thus set clearly corresponds to the actual flow rate and the reproducibility of the flow rate setting is satisfactorily achieved. As a consequence, the present invention is advantageously applicable to a small-sized apparatus, for example, particularly to a portable infusion pump.

While the present invention has been described with reference to the particular illustrative embodiment, it is not to be restricted by the embodiment but only by the appended claims. It is to be appreciated that those skilled in the art can change or modify the embodiment without departing from the scope and spirit of the present invention.

What is claimed is:

1. An infusion rate control apparatus for controlling an infusion pump powered by a motor, comprising:
   driving means for driving the motor of the infusion pump in response to a control signal;
   speed setting means, including a dual in-line package code switch having a control knob that is manually operated to set in said speed setting means a decimal value corresponding to a desired speed of the motor, for producing a binary-coded signal in dependence upon the decimal value set therein, the dual in-line package code switch and the control knob together providing a visual indication representative of a flow rate at which the liquid is to be transported;
   control signal producing means, interconnected with said speed setting means, for producing the control signal in dependence upon the binary coded signal and supplying the control signal to said driving means.

2. An apparatus according to claim 1, wherein said control signal producing means comprises:
   means for supplying a reference voltage; and
   an operational amplifier circuit, having a first input port adapted for receiving the binary-coded signal and a second input port connected to receive the reference voltage, for producing the control signal in dependence upon the binary-coded signal, said operational amplifier circuit having an output port connected to said driving means to deliver the control signal to said driving means.

3. An infusion pump comprising:
   pump means, having a motor, for transporting a liquid;
   driving means for driving the motor in response to a control signal;
   speed setting means, including a dual in-line package code switch having a control knob that is manually operated to set in said speed setting means a decimal value corresponding to a desired speed of the motor, for producing a binary-coded signal in dependence upon the decimal value set therein, the dual in-line package code switch and the control knob together providing a visual indication representative of a flow rate at which the liquid is to be transported; and
   decoder means, interconnected with said speed setting means, for decoding the binary-coded signal to produce the control signal in dependence upon the binary-coded signal and supplying the control signal to said driving means.

4. An apparatus according to claim 3, wherein said decoder means comprises:
   means for supplying a reference voltage; and
   an operational amplifier circuit, having a first input port adapted for receiving the binary-coded signal and a second input port connected to receive the reference voltage, for producing the control signal in dependence upon the binary-coded signal, said operational amplifier circuit having an output port connected to said driving means to deliver the control signal to said driving means.

5. An infusion pump according to claim 3, wherein said pump means comprises a roller pump, which is connected to the motor.

* * * * *